United States Patent [19]
Rodriguez

[11] Patent Number: 5,944,021
[45] Date of Patent: *Aug. 31, 1999

[54] THERAPEUTIC USE OF A CARBONIC ANHYDRASE ENZYME INHIBITOR FOR THE TREATMENT OF BRAIN EDEMA

[76] Inventor: Victorio C. Rodriguez, 7791 Hoertz Rd., Parma, Ohio 44134

[*] Notice: This patent is subject to a terminal disclaimer.

[21] Appl. No.: 09/023,062

[22] Filed: Feb. 13, 1998

Related U.S. Application Data

[63] Continuation-in-part of application No. 08/490,110, Jun. 7, 1995, Pat. No. 5,755,237.

[51] Int. Cl.⁶ .................................... A61B 19/00
[52] U.S. Cl. ............................................. 128/898
[58] Field of Search ............. 128/897–98; 514/869–871

[56] References Cited

U.S. PATENT DOCUMENTS

| | | |
|---|---|---|
| 4,463,208 | 7/1984 | Cragoe, Jr. et al. ..................... 562/462 |
| 4,465,850 | 8/1984 | Cragoe, Jr. et al. ..................... 562/462 |
| 5,389,630 | 2/1995 | Sato et al. ................................ 514/218 |

*Primary Examiner*—John P. Lacyk
*Attorney, Agent, or Firm*—Donald A. Bergquist

[57] ABSTRACT

A method for treating victims of cerebral edema is presented that includes the intravenous injection of a carbonic anhydrase enzyme inhibitor that passes through the blood-brain barrier, such as acetazolamide (A.K.A., DIAMOX®), which is a readily-available and often-prescribed diuretic. Such edema, or brain swelling may be caused as a result of ischemic strokes especially, but also swelling due to tumors, surgeries, or cerebral trauma. It is preferred to combine the a carbonic anhydrase enzyme inhibitor therapy with hyperventilation of the lungs, even including the use of supplemental oxygen, thereby to reduce the concentration of carbon dioxide in the blood and hence in the brain.

20 Claims, No Drawings

THERAPEUTIC USE OF A CARBONIC ANHYDRASE ENZYME INHIBITOR FOR THE TREATMENT OF BRAIN EDEMA

This application is a Continuation-in-Part of application Ser. No. 08/490,110, filed Jun. 07, 1995, now U.S. Pat. No. 5,755,237 and included herein by reference.

INTRODUCTION

This invention relates to the medical treatment of victims of cerebral edema, and especially to the relief of brain swelling as a result of ischemic strokes especially, but also swelling due a to tumors, surgeries, or cerebral trauma, which swelling usually results in severe disability and often death of the patient. More particularly, this invention relates to the therapeutic use of a carbonic anhydrase enzyme inhibitor that passes through the blood-brain barrier, such as acetazolamide as a medication to relieve such brain swelling or edema. Acetazolamide is a commonly-prescribed diuretic distributed under the trade names DIAMOX® acetazolamide SEQUELS® sustained release capsules, DIAMOX® acetazolamide tablets, and DIAMOX® sterile acetazolamide sodium parenteral (supplied as a sodium salt). DIAMOX® and SEQUELS® are registered trade marks of Lederle Laboratories Division of American Cyanamid Company.

Ischemic strokes are the result of a sudden compromising of the blood supply to the brain, that often causes brain cell swelling, abnormal electric discharges from the brain, and brain death. Whereas the causative factor in the compromising of the blood supply to the brain may be transient, as small emboli that occlude a vessel and then pass on, allowing blood flow to be reestablished. How often such transient ischemic attacks result in completed stroke (i.e., with no immediate progression or regression of symptoms) is unknown. Some patients with such attacks develop strokes; in others, the symptoms disappear without sequelae. Even transient ischemic attacks can produce brain cell swelling, a symptom that carries its own potential death threat.

PRIOR ART

Today's management of stroke involves several steps that are taken as the need becomes apparent:

a. Airway support and ventilatory assistance are given to patients with depressed levels of consciousness; supplemental oxygen is used for hypoxic patients.

b. Caution is recommended in the use of any antihypertensive agents.

c. The Stroke Council of the American Heart Association disapproved the use of corticosteroids for cerebral edema and increased intracranial pressure after stroke, noting that conventional and large doses of corticosteroids in clinical trials showed no improvement.

d. Osmotherapy and hyperventilation are recommended for patients whose condition is deteriorating as a secondary effect to increased intracranial pressure.

e. The Stroke Council stressed that data about the safety and efficacy of heparin in ischemic strokes was insufficient and conflicting, potentially dangerous, noting the frequency of parenchymal hemorrhage.

f. The panel also refused to recommend the use of nimodipine, barbiturates, naloxone, glutamate antagonists, or amphetamines.

U.S. Pat. No. 5,389,630 was issued Feb. 14, 1995, to Sato, et al., claiming an array of certain diamine compounds and their use for treating disorders of cerebral function or preventing the progress of such disorders, including cerebral hemorrhage, cerebral infarction, subarachnoid hemorrhage, transient ischemic attack, cerebrovascular disorders, and the like. The Sato et al. patent illustrates efficacy by means of tests on animals.

Prior art is available (U.S. Pat. Nos. 4,463,208, Cragoe, Jr. et al. and 4,463,850, Cragoe, Jr. et al.) that teaches the use of acetolamide in treating animal subjects suffering from brain edema caused by trauma, but it is known that human subjects differ from animal subjects in that the blood-brain barrier in humans is quite complete, as compared with that of animals. This blood-brain barrier is effective in blocking bloodstream chemicals and many medications from reaching and affecting the cells of the brain. In contrast, the blood-brain barrier in animals is incomplete. Thus, results of testing of chemicals that affect the brain cells of animals do not necessarily translate directly to results that would be obtained in human testing.

Accordingly, cerebral protective drugs that promise excellent clinical effect and are readily available and useful for oral or intravenous administration are to be desired. Applicant believes that the present invention meets that need.

DETAILED DESCRIPTION OF THE INVENTION

It is believed that at least part of the damage done during brain edema from ischemic stroke and other trauma is due to the formation of bicarbonates in the cells, which reaction is accelerated by the presence of carbonic anhydrase. Inhibitors for carbonic anhydrase are known: acetazolamide and dichlorophenamide are among them. The former is a commonly-prescribed diuretic, especially useful for short-term use, as its effectiveness diminishes after 2 or 3 days. It is marketed under the trade name DIAMOX® by Lederle Laboratories Division of American Cyanamid Company. The simplified chemical formula for acetazolamide is $C_4H_6N_4O_3S_2$ and the chemical name that is believed to abide by the naming rules of the International Union of Chemistry is:

N-(5-sulfamoyl-1,3,4-thiadiazol-2-yl)-acetamide

Acetazolamide, as an enzyme inhibitor, acts specifically on carbonic anhydrase, the enzyme that catalyzes the reversible reaction involving the hydration of carbon dioxide and the dehydration of carbonic acid:

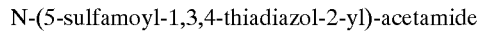
$$H_2O + CO_2 \leftrightarrows H^+ + HCO_3^-$$
Equation 1

Affecting this reaction is said to be the source of the diuretic effect in the kidney. The result is renal loss of bicarbonate (i.e., 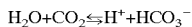$HCO_3^-$) ion, which carries out sodium, water, and potassium.

In addition, there are reports of evidence seems to indicate that acetazolamide does have utility as an adjuvant in the treatment of certain dysfunctions of the central nervous system (e.g., epilepsy). Inhibition of carbonic anhydrase in this area appears to retard abnormal, paroxysmal excessive discharge from central nervous system neurons. No prior art is known that would suggest the use of these carbonic anhydrase enzyme inhibitors specifically for the treatment of human stroke victims, or human victims of other cerebral swelling or trauma. Nothing indicates that acetazolamide would be a cerebral protective drug of value in treating such human victims.

The efficacy of this therapeutic treatment would likely be considered by medical researchers to be anecdotal, not being a part of a statistically-designed double-blind clinical experiment, but the success rate in the last-resort use of acetazolamide on patients who were otherwise thought to be terminal, has led this investigator to seek patent protection for the treatment method.

Results from twelve patients having various brain disorders who were, as a last resort, treated with intravenous injections of a solution containing 500 mg of acetazolamide in 5 ml of sterile water. Initially, the dosage administered was 2.5 ml of this solution; eventually, the full 5 ml injection was used. The injections were continued daily for 2–3 days. This treatment was used with hyperventilation of the lung (even using supplemental oxygen), thereby to reduce the carbon dioxide ($CO_2$) content and raise the oxygen ($O_2$) content in the blood and hence in the brain—whether or not the patient had been hypoxic—and diuresis to remove excess water (a further effect of the acetazolamide, although other diuretics may be employed). The goal was to drive the reversible reaction of Equation 1 to the left, thereby to reduce the amount of bicarbonate ion formed and to slow further formation of bicarbonate. The twelve cases cited included: six cerebral infarctions, one of which exhibited acute hydrocephali; two intracranial hemorrhages; one malignant meningiomas; one other tumor that involved a brain hematoma; one anoxic encephalopathic coma; and one case of thyroid coma with brain swelling. Those cases involving tumors that were removed included post-surgical edema. All patients survived the crisis that prompted the last-resort treatment with acetazolamide. All were believed to be in terminal stages of their respective crisis situations, allowing for emergency measures in an attempt to prolong life. No patients treated by this method during this period of testing did not show improvement and ultimate recovery from the respective crisis conditions.

Based upon the limited experience cited above, the method for treatment of ischemic stroke that is sought to be protected comprises the initial administration of a carbonic anhydrase enzyme inhibitor that passes through the blood-brain barrier, such as acetazolamide, by intravenous injection and additional doses of said carbonic anhydrase enzyme inhibitor that is either administered orally (i.e., by ingestion) or injected intravenously. In the preferred mode, the use of acetazolamide is combined with continued hyperventilation of the lungs. Diuresis, using a diuretic other than a carbonic anhydrase enzyme inhibitor, is recommended. Dosage of acetazolamide to be recommended may vary depending upon the perceived severity of the ischemic stroke as well as upon body weight of the patient, but an initial dose of between 250 and 500 mg with supplemental doses of between 250 and 500 mg per day, administered orally (i.e., by ingestion) or by injection, are believed to be efficacious. The dosage suitable for other carbonic anhydrase enzyme inhibitors well depend upon their efficacy or potency for this use.

Having described this invention, including the citing of functional specific examples thereof, applicant desires to include within the scope of his invention those improvements that would be immediately obvious to one skilled in the art, some, but not all of which improvements may have been referred to herein. Applicant desires the breadth of his invention to be limited only by the scope of the claims appended hereto.

I claim:

1. A therapeutic medical method of treatment of a human patient suffering from the effects of brain edema, said method comprising administering a carbonic anhydrase enzyme inhibitor that passes through the blood-brain barrier to said human patient.

2. The method of claim 1 wherein said administering a carbonic anhydrase enzyme inhibitor is by intravenously injecting a mixture comprising said carbonic anhydrase enzyme inhibitor and sterile water.

3. The method of claim 2 wherein said mixture comprises approximately 500 milligrams of a carbonic anhydrase enzyme inhibitor and approximately 5 milliliters of sterile water.

4. The method of claim 2 wherein said mixture is a solution, said carbonic anhydrase enzyme inhibitor is a solute, and said water is a solvent.

5. The method of claim 2 wherein said mixture comprises approximately 250 to 500 milligrams of a carbonic anhydrase enzyme inhibitor and approximately 2.5 to 5 milliliters of sterile water.

6. The method of claim 5 wherein said mixture is a solution, said carbonic anhydrase enzyme inhibitor is a solute, and said water is a solvent.

7. The method of claim 1 wherein said administering a carbonic anhydrase enzyme inhibitor is accomplished by medicating said patient by ingestion.

8. The method of claim 1 wherein a first dose of said carbonic anhydrase enzyme inhibitor is administered by intravenously injecting a mixture comprising said carbonic anhydrase enzyme inhibitor and sterile water and administering a subsequent dose of said carbonic anhydrase enzyme inhibitor by ingestion.

9. The method of claim 1, 2, 7, or 8 wherein said administering said carbonic anhydrase enzyme inhibitor is combined with hyperventilating the patient.

10. The method of claim 9 wherein said hyperventilating comprises increasing the concentration of oxygen in respiratory air.

11. A therapeutic medical method of treatment of a human patient suffering from the effects of brain edema specifically caused by ischemic stroke, said method comprising administering a carbonic anhydrase enzyme inhibitor that passes through the blood-brain barrier to said human patient.

12. The method of claim 11 wherein said administering said carbonic anhydrase enzyme inhibitor is by intravenously injecting a mixture comprising said carbonic anhydrase enzyme inhibitor and sterile water.

13. The method of claim 12 wherein said mixture comprises approximately 500 milligrams of said carbonic anhydrase enzyme inhibitor and approximately 5 milliliters of sterile water.

14. The method of claim 12 wherein said mixture is a solution, said carbonic anhydrase enzyme inhibitor is a solute, and said water is a solvent.

15. The method of claim 12 wherein said mixture comprises approximately 250 to 500 milligrams of said carbonic anhydrase enzyme inhibitor and approximately 2.5 to 5 milliliters of sterile water.

16. The method of claim 15 wherein said mixture is a solution, said carbonic anhydrase enzyme inhibitor is a solute, and said water is a solvent.

17. The method of claim 11 wherein said administering said carbonic anhydrase enzyme inhibitor is accomplished by medicating said patient by ingestion.

18. The method of claim 11 wherein a first dose of said carbonic anhydrase enzyme inhibitor is administered by intravenously injecting a mixture comprising said carbonic anhydrase enzyme inhibitor and sterile water and administering a subsequent dose of said carbonic anhydrase enzyme inhibitor by ingestion.

19. The method of claim 11, 12, 17, or 18 wherein said administering said carbonic anhydrase enzyme inhibitor is combined with hyperventilating the patient.

20. The method of claim 19 wherein said hyperventilating comprises increasing the concentration of oxygen in respiratory air.

* * * * *